(12) United States Patent
Todd et al.

(10) Patent No.: US 10,871,458 B2
(45) Date of Patent: Dec. 22, 2020

(54) RADIO FREQUENCY MEASUREMENT DEVICE FOR MEASURING GRAIN LOSS

(71) Applicant: Deere & Company, Moline, IL (US)

(72) Inventors: William D. Todd, Bettendorf, IA (US); Gurmukh H. Advani, West Fargo, ND (US); Noel W. Anderson, Fargo, ND (US)

(73) Assignee: DEERE & COMPANY, Moline, IL (US)

( * ) Notice: Subject to any disclaimer, the term of this patent is extended or adjusted under 35 U.S.C. 154(b) by 34 days.

(21) Appl. No.: 16/165,368

(22) Filed: Oct. 19, 2018

(65) Prior Publication Data

US 2019/0137416 A1    May 9, 2019

Related U.S. Application Data

(60) Provisional application No. 62/581,797, filed on Nov. 6, 2017.

(51) Int. Cl.
*G01N 22/00* (2006.01)
*A01D 41/127* (2006.01)
*G01N 33/02* (2006.01)

(52) U.S. Cl.
CPC ......... *G01N 22/00* (2013.01); *A01D 41/1273* (2013.01); *G01N 33/025* (2013.01)

(58) Field of Classification Search
CPC .. A01D 41/1273; G01N 22/00; G01N 33/025; G01F 1/66; G01F 1/76
See application file for complete search history.

(56) References Cited

U.S. PATENT DOCUMENTS

| 4,253,471 A | 3/1981 | Klimmer |
| 4,311,957 A | 1/1982 | Hewitt et al. |
| 4,782,282 A | 11/1988 | Bachman |
| 4,806,847 A | 2/1989 | Atherton et al. |
| 5,057,848 A | 10/1991 | Rankin et al. |

(Continued)

FOREIGN PATENT DOCUMENTS

| EP | 843959 A1 | 5/1998 |
| EP | 940656 A1 | 9/1999 |

(Continued)

OTHER PUBLICATIONS

European Search Report issued in counterpart application No. 18204751.4 dated Jun. 19, 2019. (7 pages).

(Continued)

*Primary Examiner* — Jay Patidar (57) ABSTRACT

Transmit patches lie on the outer set of conductive patches that are coupled to the transmitter via the signal splitter. The receive patches lie on the outer set of conductive patches that are coupled to one or more receivers to receive a radio frequency field (e.g., fringing field) associated with the transmitted signal of one or more adjacent corresponding transmit patches. A detector is associated with one or more respective receivers for determining or estimating an attenuation of the radio frequency field (e.g., fringing field). An electronic data processor is arranged for evaluating the estimated attenuation to estimate the grain loss content and material other than grain content of the agricultural material.

20 Claims, 6 Drawing Sheets

(56) References Cited

U.S. PATENT DOCUMENTS

| | | | |
|---|---|---|---|
| 5,708,366 A * | 1/1998 | Nelson | G01N 22/04 |
| | | | 324/601 |
| 6,681,551 B1 | 1/2004 | Sheidler et al. | |
| 6,921,330 B2 | 7/2005 | Grywacheski et al. | |
| 7,068,050 B2 | 6/2006 | Steele et al. | |
| 7,804,588 B2 | 9/2010 | Kormann et al. | |
| 8,410,793 B2 | 4/2013 | Armbruster et al. | |
| 8,629,681 B1 * | 1/2014 | Trabelsi | G01N 22/04 |
| | | | 324/637 |
| 9,494,538 B2 | 11/2016 | Kozicki et al. | |
| 9,924,636 B2 | 3/2018 | Lisouski et al. | |
| 2004/0183718 A1 | 9/2004 | Hagg | |
| 2005/0026662 A1 | 2/2005 | Fechner et al. | |
| 2006/0214835 A1 | 9/2006 | Lee et al. | |
| 2007/0106172 A1 | 5/2007 | Abreu | |
| 2013/0141115 A1 | 6/2013 | Bourely et al. | |
| 2014/0230580 A1 | 8/2014 | Dybro et al. | |
| 2014/0326066 A1 | 11/2014 | Mears | |
| 2014/0331631 A1 | 11/2014 | Sauder et al. | |
| 2015/0293029 A1 | 10/2015 | Acheson et al. | |
| 2016/0330907 A1 | 11/2016 | Anderson et al. | |
| 2017/0065464 A1 | 3/2017 | Heil et al. | |
| 2018/0059034 A1 * | 3/2018 | Advani | G01F 25/003 |

FOREIGN PATENT DOCUMENTS

| | | |
|---|---|---|
| EP | 3299773 A1 | 3/2018 |
| WO | 9849529 A1 | 11/1998 |

OTHER PUBLICATIONS

European Search Report issued in counterpart application No. 18204750.6 dated Jun. 21, 2019. (8 pages).

Milligan, Thomas A. Modem Antenna Design, Second Edition. John Wiley & Sons, 2005. p. 299-300.

Yeow, You; Abbas, Zulkifly; and Khalid, Kaida. "Application of Microwave Moisture Sensor for Determination of Oil Palm Fruit Ripeness." Measurement Science Review, vol. 10, No. 1, Jan. 2010, pp. 7-14. DOI: <https://doi.org/10.2478/v10048-010-0002-x>.

* cited by examiner

RADIO FREQUENCY MEASUREMENT DEVICE FOR MEASURING GRAIN LOSS

RELATED APPLICATION

This document (including the drawings) claims priority and the benefit of the filing date based on U.S. provisional application No. 62/581,797, filed Nov. 6, 2017 under 35 U.S.C. § 119 (e), where the provisional application is hereby incorporated by reference herein.

FIELD

This disclosure related to a measurement device for measuring grain loss associated with a harvester or combine machine.

BACKGROUND

In a harvester or combine, grain is separated from other harvested agricultural material, which may be referred to as material other than grain (MOG). For example, for corn or maize grain refers to the kernels that are isolated from MOG, such as stover, stalks, leaves, husks, chaff, and corn cobs. Grain loss refers to the volume, mass, percentage, fraction or other amount of harvested grain that the combine or harvester does not separate from MOG or other harvested agricultural material. In the combine, most of the harvested grain is directed to a grain tank, grain storage area or a cart the follows the combine. Meanwhile, the MOG is distributed from the rear of the combine as it harvests the crop. The grain loss can include a measure of the volume or amount of grain mixed in or comingled with the MOG after the separator or cleaning shoe of the combine. For example, the residue management system of the combine directs the MOG and comingled grain loss (e.g., nominal grain loss in a properly functioning and adjusted combine) to exit the rear of the combine for distribution on the field, rather than being distributed as feed for animals, food for human consumption or feedstock for ethanol production.

By prompt, automatic real-time adjustment of combine settings, the combine or harvester has the potential to reduce grain loss commingled with the MOG or residue distributed on the field. Thus, there is a need for a measurement device for measuring accurately, rapidly (e.g., in real time) and dynamically the grain loss associated with operation of a combine or harvester, as the combine progresses through a field during a harvesting of crop.

SUMMARY

In accordance with one aspect of the disclosure, a measurement device comprises a transmitter for providing a transmitted signal. A signal splitter splits the transmitted signal into transmitted signal components. A set of planar antenna panels are spaced apart and are parallel to each other to provide a channel for agricultural material to flow above or below the set of planar antenna panels. Each antenna panel comprises a dielectric planar member associated with conductive patches. Each dielectric planar member has an upper side and a lower side. An outer set of conductive patches lies on one of the outer sides of the set of planar dielectric layers. For example, transmit patches lie on the outer set of planar dielectric layers and are coupled to the transmitter via the signal splitter. Receive patches lie on the outer set of planar dielectric layers and are coupled to one or more receivers to receive a radio frequency field (e.g., fringing field) associated with the transmitted signal of one or more adjacent corresponding transmit patches. A detector is associated with one or more respective receivers for determining or estimating an attenuation, phase shift, or both of the radio frequency field (e.g., fringing field). An electronic data processor is arranged for evaluating the estimated attenuation, phase shift, or both to estimate the grain loss content and material other than grain content of the agricultural material.

BRIEF DESCRIPTION OF THE DRAWINGS

Like reference numbers in any set of two or more drawings indicates like elements.

BRIEF DESCRIPTION

In accordance with one aspect of the disclosure in FIG. 1 through FIG. 4, inclusive, a measurement device 11 comprises a transmitter 10 for providing a transmitted signal. A signal splitter 12 splits the transmitted signal into transmitted signal components. A set of substantially planar antenna panels 38 are spaced apart and are parallel to each other to provide one or more channels 16 for agricultural material to flow above, below or between the set of planar antenna panels 38. Each antenna panel 38 comprises a planar dielectric layer 14 associated with conductive patches (26, 28). Accordingly, a set of substantially dielectric layers 14 are spaced apart and are parallel to each other to provide one or more channels 16 for agricultural material to flow above, below or between the set of dielectric layers 14.

Figure 1:
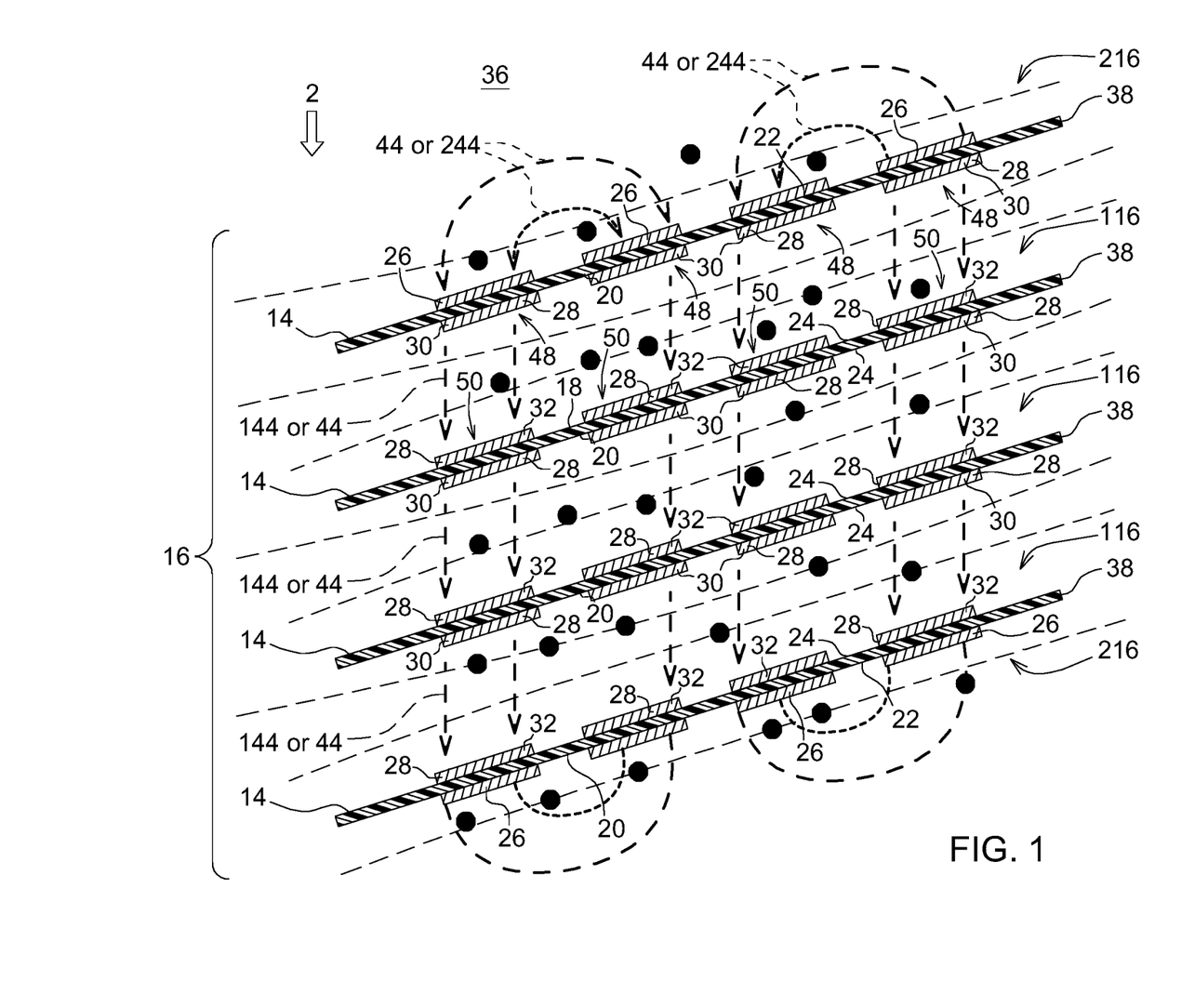
FIG. 1 is a cross-sectional view of an antenna assembly of a measurement device in accordance with the disclosure.

Each dielectric planar layer 14 has an upper side 18 and a lower side 20. For example, an outer set of secondary conductive patches 26 lies on one of the outer sides 22 of the set of planar dielectric layers 14. Transmit patches 30 lie on the outer set of planar dielectric layers 14 and are coupled to the transmitter 10 via the signal splitter 12. The receive patches 32 lie on the outer set of planar dielectric layers 14 that are coupled to one or more receivers 34 to receive a radio frequency field 44 (e.g., fringing field or secondary field 244) associated with the transmitted signal of one or more adjacent corresponding transmit patches 30.

Figure 4:
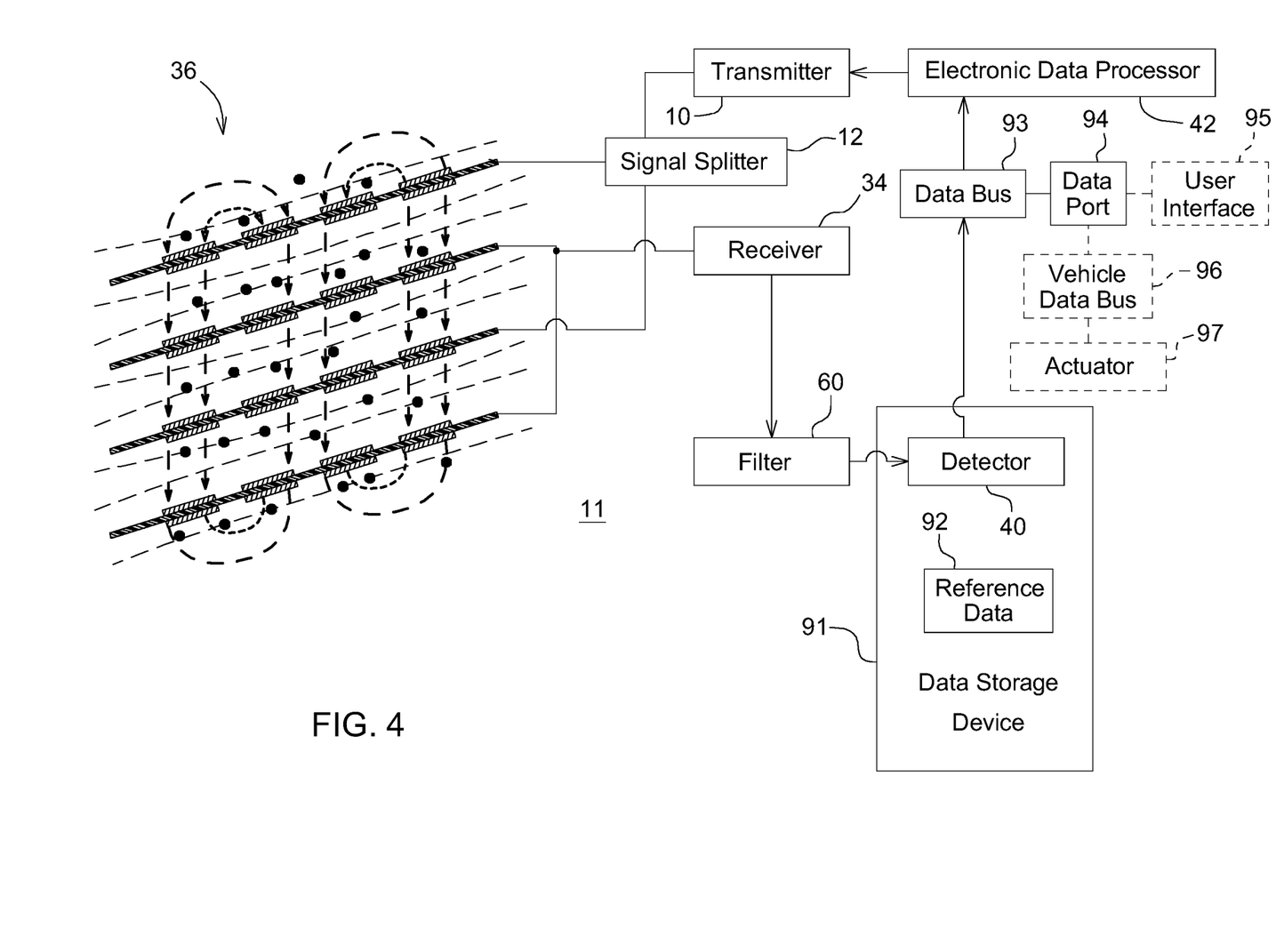
FIG. 4 shows one embodiment of a block diagram and side view of the antenna assembly of the measurement device in accordance with FIG. 1.

A detector 40 is associated with one or more respective receivers 34 for determining or estimating an attenuation, or a phase change, or both of the radio frequency fields 44 (e.g., primary field 144, or fringing field, or secondary field 244, or both). An electronic data processor 42 is arranged for evaluating the estimated attenuation, estimated phase change, or both to estimate the grain loss content and material other than grain (MOG) content of the agricultural material. In this document, phase shift and phase change of the radio frequency (e.g., microwave) field or the transmitted signal between any transmit patch 30 (or transmit patch array) and a corresponding receive patch 32 (or receive patch array) shall be regarded synonymous terms. Grain loss content is a mass, weight, or volumetric measurement of the grain loss or combine-processing yield loss of (grain, seed, fiber, or the like within) the harvested agricultural material. In this document, grain loss may refer generally to combine-processing yield loss of grain, corn, maize, soybeans, beans, oats, wheat, cotton, seed, fiber, or the like.

In one configuration, grain loss is a function of the dielectric impedance of MOG and the dielectric impedance of grain in the harvested agricultural material. Alternately, the grain loss is proportional to a function of the observed radio frequency attenuation (e.g., microwave) and/or phase shift of MOG and the observed radio frequency (e.g., microwave) attenuation of grain and/or phase shift in the harvested agricultural material. For example, grain loss ($G_L$) may be determined in accordance with the following equation:

$$G_L = (Z_{dielectric,MOG} + Z_{dielectric,Grain}) / Z_{dielectric,MOG},$$

where $Z_{dielectric,MOG}$ is the dielectric impedance of MOG in the channel 16 or channels 16 (e.g., primary channel 116 and secondary channel 216), and $Z_{dielectric,Grain}$ is the dielectric impedance of grain in the channel 16 or channels (e.g., primary channel 116 and secondary channel 216). The primary channels 116 are defined by the spatial area between the substantially planar antenna panels 38, whereas the secondary channels 216 are defined by the spatial area above and below the outer planar antenna panels 38. As the harvested agricultural material flows within the primary channels 116, the secondary channels 216, or both the measurement device 11 can measure the observed radio frequency (e.g., microwave) attenuation and/or phase shift of MOG and the observed radio frequency (e.g., microwave) attenuation and/or phase shift of grain in the harvested agricultural material to facilitate estimation of the grain loss.

In FIG. 1 through FIG. 4, inclusive, the substantially planar antenna panels 38 comprise planar dielectric layers 14 that are associated with conductive patches (26, 28) and respective conductive traces (31, 33) overlying the dielectric layer 14. In one embodiment, the planar dielectric layer 14 comprises a dielectric substrate of a circuit board. For example, the dielectric layer 14 is composed of a plastic, polymeric, composite (e.g., fiber-filled polymeric or plastic matrix) or ceramic material. The dielectric layer 14 combined with the conductive patches (26, 28) may comprise a circuit board or a double-sided circuit board with metallic conductive patches (26, 28) that are connected to conductive traces (31, 33), such as stripline, microstrip, or other transmission line. In alternate embodiments, the stripline, microstrip or other transmission line may be replaced with or augmented with coaxial cable.

In one embodiment, conductive patches are characterized as primary conductive patches 28 and secondary conductive patches 26, where the secondary conductive patches 26 comprise an outer set of conductive patches on the antenna assembly 36 and where the primary conductive patches 28 comprise an inner set of conductive patches on the antenna assembly 36. The conductive patches (26, 28) are composed of a metal, metal alloy or a metallic layer that is electrically conductive and suitable for operation at radio frequencies (e.g., microwave frequencies).

Figures 2, 3:
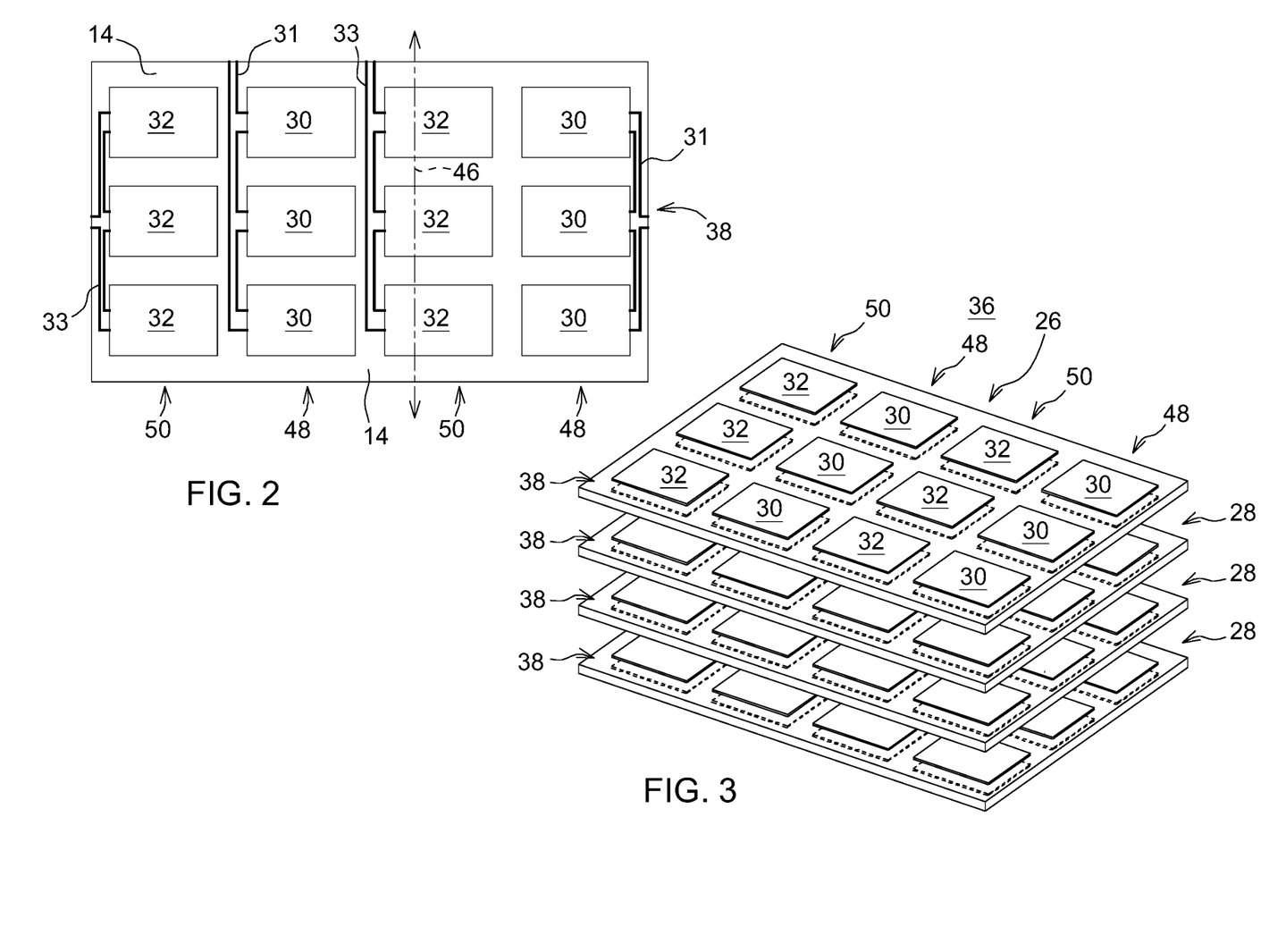
FIG. 2 shows a plan view of an illustrative embodiment of an antenna assembly viewed from the perspective of reference arrow 2 of FIG. 1.
FIG. 3 shows a perspective view of the antenna assembly comprising a set of planar antenna panels.

One or more columns or rows of conductive patches (26, 28) can form a transmitting antenna or a receiving antenna, such as an antenna array that is coupled to transmission line. In particular, each column, row or other group of conductive patches (26, 28) is coupled by transmission line as an antenna array, where the transmission line matches or coordinates the impedance and phase of radio frequency signals of the conductive patches in the antenna array. As illustrated in FIG. 2, a transmitting antenna comprises a set of transmit patches 30 in a transmit row 48, or transmit column, that are fed by a strip or conductive trace 31, such as stripline, microstrip, or other transmission line. Similarly, a receiving antenna comprises a set of receive patches 32 in a receive row 50, or receive column, that are coupled to a strip or conductive trace 33, such as stripline, microstrip, or other transmission line. In one configuration, each planar antenna panel 38 comprises a circuit board, which has the dielectric layer 14, the associated conductive patches (26, 28) on one or both sides (18, 20), and associated conductive traces (31, 33) on one or both sides.

In one embodiment, the antenna assembly 36, can be configured to occupy an entire internal width, or a portion of the internal width, of the combine 52 or harvester, such as the internal width of the internal processing system for agricultural material after the kernel processing system or the grain processing system; namely, the internal width of the separator, the stray chopper, the cleaning shoe, sieve, residue distribution system, or the like. For example, the antenna assembly 36 can be configured to occupy an entire internal width, or a portion of the internal width, of the combine 52 or harvester in the tailboard assembly area or near a frog-mouth assembly. In one configuration, the planar antenna panels 38 or the planar dielectric layers 14 are arranged as a series of parallel louvers that are separated by primary channels 116 (e.g., three primary channels as illustrated in FIG. 1) in the path of harvested material other that grain (MOG) and grain loss. Similarly, the secondary channels 216 are above and below the antenna assembly 36 or outer sides 22 of the antenna assembly 36. The primary channels 116, the secondary channels 216, or both are disposed between the kernel processing module and the exit port 54 from the rear of the combine 52 that can be used to distribute MOG or residue on the field during harvesting (e.g., in accordance with standard agricultural practices).

For the outer set of the secondary conductive patches 26 that lie on the outer sides 22 of the set of the planar dielectric layers 14 or antenna assembly 36, the transmit patches 30 are substantially co-planar to the receive patches 32, as illustrated in FIG. 1, FIG. 2 and FIG. 3. In one embodiment, the outer set of secondary conductive patches 26 on one of the outer sides 22 of the set of planar dielectric layers 14 further comprises the outer set of secondary conductive patches 26 on the outer upper side 18 of the planar dielectric layers 14 or antenna assembly 36. Similarly, the outer set of secondary conductive patches 26 on one of the outer sides 22 of the set of planar dielectric layers 14 further comprises the outer set of secondary conductive patches 26 on the lower side 20 of the planar dielectric layers 14 or antenna assembly 36.

In one configuration within each antenna panel 38, of the antenna assembly 36, the transmit patches 30 and the receive patches 32 alternate, such that each row in a lateral direction 46 within a harvester (e.g., combine 52) is exclusively a transmit row 48 or a receiving row 50. In another configuration within each antenna panel 38 of the antenna assembly 36, the transmit patches 30 and the receive patches 32 alternate, such that each aggregate array of rows of the antenna assembly within the harvester (e.g., combine 52) is exclusively an array (e.g., set) of transmit rows 48 or an array (e.g., set) of receive rows 50.

In one embodiment, on the outer sides 22 the secondary conductive patches 26 are configured as outer transmit patches 30 and the outer receive patches 32, alternately, such that each row in a lateral direction 46 within a harvester is exclusively a transmitting row 48 or a receiving row 50, as illustrated in FIG. 2 and FIG. 3. Meanwhile, on the inner sides 24 the primary conductive patches 28 are configured as the inner transmit patches 30 and the inner receive patches 32 with multiple adjacent rows (as illustrated by the arrows indicating the primary radio frequency fields 144 in FIG. 1) or alternating rows that are exclusively a transmitting row 48 and a receiving row 50.

For the inner set of primary conductive patches 28, the transmit patches 30 of or among the primary conductive patches 28 substantially face the receive patches 32 on separate planar dielectric layers 14 or separate substantially planar antenna panels 38. For the inner set of primary conductive patches 28, the inner transmit patches 30 and the inner receive patches 32 can alternate on opposites sides of one or more substantially planar members 14, such that an entire path of harvested agricultural material (MOG and grain loss) through the spatial channels of antenna assembly 36 has a plurality of rows for transmitting or a plurality of rows for receiving that are interconnected by proper conductive traces.

The inner set of primary conductive patches 28 lies on one of the inner sides 24 of the set of planar dielectric layers 14 or antenna panels 38. Further, the inner set of primary conductive patches 28 lies on the inner upper side 18 of the planar dielectric layers 14. The inner set of primary conductive patches 28 lies on one of the inner sides 24 of the set of planar dielectric layers 14 or antenna panels 38. Further, the inner set of primary conductive patches 28 lies on the inner set of conductive patches on the lower side 20 of the antenna assembly 36.

The splitter 12 may comprise a hybrid splitter, a ferrite toroidal transformer, a microstrip or stripline splitter or an impedance matching network for splitting the transmitted signal into multiple signal components for transmission to different transmit patches in one or more antenna panels 38 (e.g., double-sided circuit boards) of the antenna assembly 36.

In one embodiment, as shown in FIG. 4, a filter 60, such as a low pass filter, is coupled to one or more receivers 34. The filter 60 may represent hardware, software, or both, where filtering can be completed readily in the digital domain.

In an alternate embodiment, the filter 60 is coupled between the receive patches 32 and one or more receivers 34.

Figure 6:
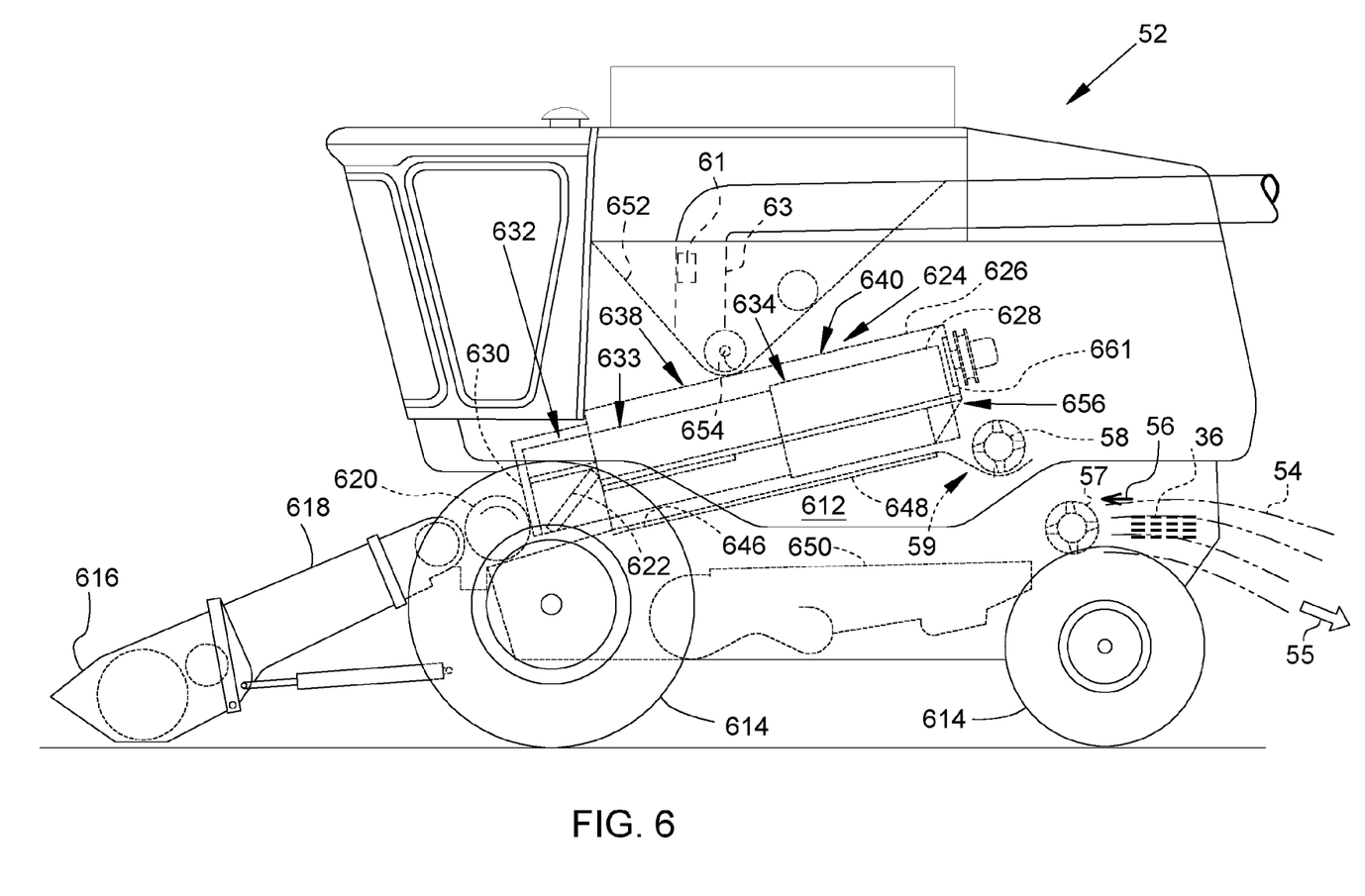
FIG. 6 is a side view of a combine with the exterior of the combine removed to better reveal its internal components and one possible mounting location of the measurement device.

The measurement device 11 or the antenna assembly 36 has various possible mounting locations with the harvester or combine 52, which may be used separately or cumulatively. In accordance with a first mounting position, the measurement device 11 or antenna assembly 36 is mounted in a combine 52 toward an exit port 54 of agricultural material from the combine 52 rearward 55 from a straw chopper 57 of the combine 52, as illustrated in FIG. 6. In accordance with a second mounting position, the measurement device 11 or antenna assembly 36 is mounted on a combine 52 frontward 56 from a straw chopper 57 and reward from a chaff discharge zone 59 or discharge beater 58 within the combine 52, as set forth in FIG. 7.

The measurement device 11 can measure the attenuation (e.g., reduction in transmitted signal strength), phase change, or both of radio frequency fields 44, such as primary radio frequency fields 144, or secondary radio frequency fields 244 (e.g., fringing fields) that are transmitted to intercept the harvested agricultural material or spatial zones in one or more primary channels 116 and secondary channels 216. The measurement device 11 can measure the harvested agricultural material in accordance with several techniques, which may be applied separately or cumulatively.

Under a first technique, the measurement device 11 can measure the attenuation, phase change or both of one or more primary radio frequency fields 144 that are transmitted to intercept the harvested agricultural material or spatial zones in one or more primary channels 116 of the antenna assembly 36. The primary radio frequency fields 144 are located between the inner sides 24 of the planar dielectric layers 14 or respective primary conductive patches 28 on the dielectric layers 14 that face each other. For example, the set of planar dielectric layers 14 is spaced apart and parallel to each other to provide a primary channel 116 for agricultural material to flow between the set of planar dielectric layers 14 or antenna panels 38. Further, an inner set of primary conductive patches 28 lie on the inner sides 24 of the set of planar dielectric layers 14 or antenna panels 38. The transmit patches 30 of the inner set of primary conductive patches 28 are coupled to the transmitter 10 via the signal splitter 12 and the receive patches 32 of the inner set of primary conductive patches 28 are coupled to one or more receivers 34 to receive the primary radio frequency field 144, between two adjoining planar dielectric layers 14 or two antenna panels 38 of the set. The primary radio frequency field 144 is associated with the transmitted signal of one or more adjacent corresponding transmit patches 30. The detector 40 is associated with one or more respective receivers 34 for determining or estimating an aggregate attenuation, phase change or both of the radio frequency field 44, such as the primary radio frequency field 144, or the secondary radio frequency field 244, or both. Finally, the electronic data processor 42 is arranged for evaluating the estimated aggregate attenuation and/or phase shift to estimate the grain loss content and material other than grain content of the harvested agricultural material.

For example, the electronic data processor 42 may refer to a look-up table or reference data 92 stored in a data storage device 91 that has, stores or retrieves any of the following reference data 92: (1) individual-channel attenuation and/or aggregate-channel (e.g., average, weighted average, or mean) attenuation versus grain loss content for the primary radio frequency field 144 for any combination of one or more primary channels 116 of the antenna assembly 36, (2) primary attenuation of the primary radio frequency field 144 versus grain loss content (e.g., for each transmit patch 30 (or transmit patch array/row/column, such as row 48) and each corresponding receive patch 32 (or each corresponding receive patch array/row/column, such as row 50) for one or more primary channels 116 of the antenna assembly 36), (3) individual-channel phase change and/or aggregate-channel (e.g., average, weighted average or mean) phase change versus grain loss content (e.g., for each transmit patch 30 (or transmit patch array/row/column, such as row 48) and each corresponding receive patch 32 (or each corresponding receive patch array/row/column, such as row 50) for one or more primary channels 116 of the antenna assembly 36), and/or (4) primary phase change of the primary radio frequency field 144 versus grain loss content (e.g., for each transmit patch 30 (or transmit patch array/row/column, such as row 48) and each corresponding receive patch 32 (or each corresponding receive patch array/row/column, such as row 50) for one or more primary channels 116 of the antenna assembly 36). Further, the measurement device 11 measures observed attenuation, observed phase change, or both consistent with, or corresponding to, the above reference data 92 to facilitate comparison, matching (e.g., within a target range or target tolerance) or correlation of the observed attenuation, observed phase change, or both with the above reference data 92 to derive or determine the observed grain loss in the channel 16, observed combine-processing yield loss in the channel 16, a similar metric, dielectric impedance of grain in the channel 16, or dielectric impedance of material other than grain in the channel 16.

Under a second technique, the measurement device 11 can measure the attenuation, phase change or both of one or more secondary radio frequency fields 244 that are transmitted to intercept the harvested agricultural material or spatial zones in one or more secondary channels 216 above or below the antenna assembly 36. The secondary radio frequency fields 244 are located above or below the outer sides 22 of the planar dielectric layers 14, antenna panels 38, or secondary conductive patches 26 on the dielectric layers 14. For example, a secondary channel 216 occupies a vertical gap or spatial zone between the antenna assembly 36 and combine interior for harvested agricultural material to flow above and below the antenna assembly 36 or the set of antenna panels 38. Further, an outer set of secondary conductive patches 26 lie on the outer sides 22 of the set of planar dielectric layers 14 or antenna panels 38. The transmit patches 30 of the outer set of secondary conductive patches 26 are coupled to the transmitter 10 via the signal splitter 12 and the receive patches 32 of the outer set of secondary conductive patches 26 are coupled to one or more receivers 34 to receive the secondary radio frequency field 244, between a pair of secondary conductive patches 26 on the outer sides 22. The secondary radio frequency field 244 is associated with the transmitted signal of one or more adjacent corresponding transmit patches 30. The detector 40 is associated with one or more respective receivers 34 for determining or estimating an aggregate attenuation, phase change or both of the radio frequency field 44 or fields 44, such as the primary radio frequency field 144, or the secondary radio frequency field 244, or both. Finally, the electronic data processor 42, the detector 40, or the measurement device 11 is arranged for evaluating the estimated aggregate attenuation, or aggregate phase change, or both to estimate the grain loss content and material other than grain content of the harvested agricultural material.

For example, the electronic data processor 42 may refer to a look-up table or reference data 92 stored in a data storage device 91 that has, stores or retrieves any of the following reference data 92: (1) individual-channel attenuation versus grain loss content and/or aggregate-channel (e.g., average, weighted average, or mean) attenuation versus grain loss content for the secondary radio frequency field 244 for any combination of one or more secondary channels 216 of the antenna assembly 36, (2) secondary attenuation of the secondary radio frequency field 244 versus grain loss content (e.g., for each transmit patch 30 (or transmit patch array/ row/column, such as row 48) and each corresponding receive patch 32 (or each corresponding receive patch array/row/column, such as 50) for one or more secondary channels 216 of the antenna assembly 36), (3) individual-channel phase change versus grain loss content and/or aggregate-channel (e.g., average, weighted average or mean) phase change versus grain loss content (e.g., for each transmit patch 30 (or transmit patch array/row/column, such as row 48) and each corresponding receive patch 32 (or each corresponding receive patch array/row/column, such as row 50) for one or more secondary channels 216 of the antenna assembly 36), and/or (4) secondary phase change of the secondary radio frequency field 244 versus grain loss content (e.g., for each transmit patch 30 (or transmit patch array/row/column, such as row 48) and each corresponding receive patch 32 (or each corresponding receive patch array/row/column, such as row 50) for one or more secondary channels 216 of the antenna assembly 36). Further, the measurement device 11 measures observed attenuation, observed phase change, or both consistent with, or corresponding to, the above reference data 92 to facilitate comparison, matching (e.g., within a target range or target tolerance) or correlation of the observed attenuation, observed phase change, or both with the above reference data 92 to derive or determine the observed grain loss, a similar metric, the observed grain loss in the channel 16, observed combine-processing yield loss in the channel 16, a similar metric, dielectric impedance of grain in the channel 16, or dielectric impedance of material other than grain in the channel 16.

Under the third technique, the first and second techniques are combined to measure individual-channel contributions and/or aggregate-channel contributions of attenuation, phase or both from the primary channels 116 and secondary channels 216 of the antenna assembly. For example, the electronic data processor 42 may refer to a look-up table or reference data 92 stored in a data storage device 91 that has, stores or retrieves any of the following reference data: (1) individual-channel attenuation versus grain loss content and/or aggregate-channel (e.g., average, weighted average or mean) attenuation versus grain loss content for any combination of one or more channels (116, 216) of the antenna assembly 36, and/or (2) individual-channel phase change versus grain loss content and/or aggregate-channel (e.g., average, weighted average or mean) phase change versus grain loss content for any combination of one or more channels (116, 216) of the antenna assembly 36. Further, the measurement device 11 measures observed attenuation, phase change, or both consistent with, or corresponding to, the above reference data 92 to facilitate comparison, matching (e.g., within a target range or target tolerance) or correlation of the observed attenuation, phase change, or both with the above reference data 92 to derive or determine the observed grain loss, observed combine-processing yield loss in the channel 16, a similar metric, dielectric impedance of grain in the channel 16, or dielectric impedance of material other than grain in the channel 16.

In accordance with one aspect of the disclosure, a measurement device 11 comprises a transmitter 10 for providing a transmitted signal. A signal splitter 12 splits the transmitted signal into transmitted signal components. A set of planar dielectric layers 14 (or planar antenna panels 38) is spaced apart and parallel to each other to provide a primary channel 116 for agricultural material to flow between the set of planar dielectric layers 14 (or planar antenna panels 38) and a secondary channel 216 for agricultural material to flow above or below the set of planar dielectric layers 14 (or planar antenna panels 38). Collectively, the aggregate flow of agricultural material including material other than grain (MOG) and grain (e.g., lost grain or grain loss) is the sum of flows of agricultural material associated with the primary channel 116 and the secondary channel 216. Each dielectric planar member has an upper side 18 and a lower side 20.

An inner set of primary conductive patches 28 lie on the inner sides 24 of the set of planar dielectric layers 14 or antenna panels 38. The transmit patches 30 of the inner set of primary conductive patches 28 are coupled to the transmitter 10 via the signal splitter 12 and the receive patches 32 of the inner set of primary conductive patches 28 are coupled to one or more receivers 34 to receive a radio frequency field associated with the transmitted signal of one or more adjacent corresponding transmit patches 30.

An outer set of secondary conductive patches 26 lies on one of the outer sides 22 of the set of planar dielectric layers 14 or antenna panels 38. Transmit patches 30 lie on the outer set of secondary conductive patches 26 that are coupled to the transmitter 10 via the signal splitter 12. The receive patches 32 lie on the outer set of secondary conductive patches 26 that are coupled to one or more receivers 34 to receive a radio frequency field (e.g., fringing field 44) associated with the transmitted signal of one or more adjacent corresponding transmit patches 30.

In one embodiment, the antenna panels 38, the dielectric layers 14, the conductive patches (26, 28) and conductive traces (31, 33) are coated with a dielectric protective coating to protect the antenna panels 38 from abrasion from the harvested agricultural material or contaminants therein, such as small pebbles, sand or other abrasive reside that is directed to the exit port 54 of the combine. For example, the dielectric protective coating may comprise a ceramic filler bound in a polymeric or plastic matrix or resin.

In FIG. 4, a detector 40 is associated with one or more respective receivers 34 (or a multi-channel receiver or rake receiver) for determining or estimating an attenuation, phase change or both of the radio frequency field 44 or fields 44 (e.g., fringing field, primary radio frequency field 144 or secondary radio frequency field, or both). For example, a detector 40 is associated with one or more respective receivers 34 for determining or estimating a primary attenuation, phase change, or both, of the received radio frequency field in the primary channel 116 and for determining or estimating a secondary attenuation of the radio frequency field 44 in the secondary channel 216.

In one configuration, the detector 40 is configured as a data storage device 91 and software instructions for execution by or in conjunction with the data processor 42. For example, the data detector 40 or its software instructions may implement a phase change measurement module, an attenuation measurement module, or both. To realize or provide the detector 40, the data storage device 91 comprises an electronic memory, electronic non-volatile-random-access memory, optical data storage device, a magnetic storage device or another data storage device for storing analog data or digital data, such as reference data 92 and software instructions to implement a phase change measurement module, an attenuation measurement module, or both. The data storage device 91 or detector 40 may store a look-up table or reference data 92 in a data storage device 91 that has aggregate attenuation versus grain loss content, primary attenuation of the primary radio frequency field 144 versus grain loss content, and secondary attenuation of the secondary radio frequency field 244 versus grain loss content.

In FIG. 4, an electronic data processor 42 is arranged for evaluating the estimated attenuation to estimate the grain loss content and material other than grain content of the agricultural material. For example, an electronic data processor 42 is arranged for evaluating the estimated aggregate attenuation of the primary attenuation and the secondary attenuation to estimate the grain loss content and material other than grain content of the agricultural material. The electronic data processor 42 may comprise a microcontroller, a microprocessor, a programmable logic device, a field programmable gate array, an application specific integrated circuit, a digital signal processor, a logic gate or logic circuit, or another data processing device.

In one embodiment, a data storage device 91 or detector 40 is coupled to the electronic data processor 42 via a data bus 93. For example, the data storage device 91 comprises electronic memory, nonvolatile random access electronic memory, a magnetic storage device, an optical storage device, or the like. The data storage device 91 stores a measurement of a reference signal parameter, such as a reference signal strength, an attenuation threshold or reference attenuation, a reference phase change, or other reference data 92 on signal parameters, when no harvested material is present between the transmit patch or patches and receive patch or path, or between the transmitting antenna and receiving antenna when a certain known harvested material with a known grain loss content is present between the transmit patch or patches and the receive patch or path.

The electronic data processor 42 is arranged to determine a difference or differences (e.g., an attenuation difference, a phase change difference or both) between the observed signal parameter of the transmitted signal parameter. For example, the electronic data processor 42 is arranged to compare an observed attenuation to: (1) a first look-up table, equation, graph or reference data 92 of reference attenuation to material other than grain, or (2) a second look-up table, equation, graph or reference data of reference attention to grain loss. In one embodiment, the detector 40 or the electronic data processor 42 determines that the attenuation of the transmitted signal (or received signal) varies with oil content with the dielectric material of the harvested material. If grain loss is present, there is generally greater attenuation within a certain radio frequency or microwave frequency ranges associated with the detection of the oil content in grain, kernels and seeds, or the presence of the grain, kernel and seeds.

In one embodiment, the transmitter 10 is adapted to transmit a frequency band of the transmitted signal within the range of approximately 900 MHz to approximately 6 GHz, or narrower frequency bands within the above frequency range. Similarly, the receiver 34 is adapted to receive a frequency band of the transmitted signal within the range of approximately 900 MHz to approximately 6 GHz, or narrower frequency bands within the above frequency range. For example, the detector 40 or the electronic data processor 42 may detect or estimate oil content and corresponding grain loss after the transmitter 10 transmits and the receiver 34 receives a transmitted signal within the range or band of approximately 4 GHZ to approximately 6 GHz. Meanwhile, moisture in the harvested agricultural material may be detected by transmitting a transmitted signal within the range or band of approximately 900 MHz to approximately 2.4 GHz.

During the calibration mode when no harvested material is present or when harvested material with known grain loss is present in one or more primary channels 116, one or more secondary channels 216, or both, the attenuation of the received signal at the receiver 34 is minimal and the receiver 34 receives a transmitted signal (or received signal) that meets or exceeds an attenuation threshold, reference attenuation, or reference signal strength. During an operational mode when predominately harvested material, such as stover, corn cobs, stalks, or other plant portions with high cellulose content are present, the attenuation of the transmitted signal (or received signal) is substantially equivalent to that of the calibration mode, as adjusted for moisture content of the harvested material.

Figure 7:
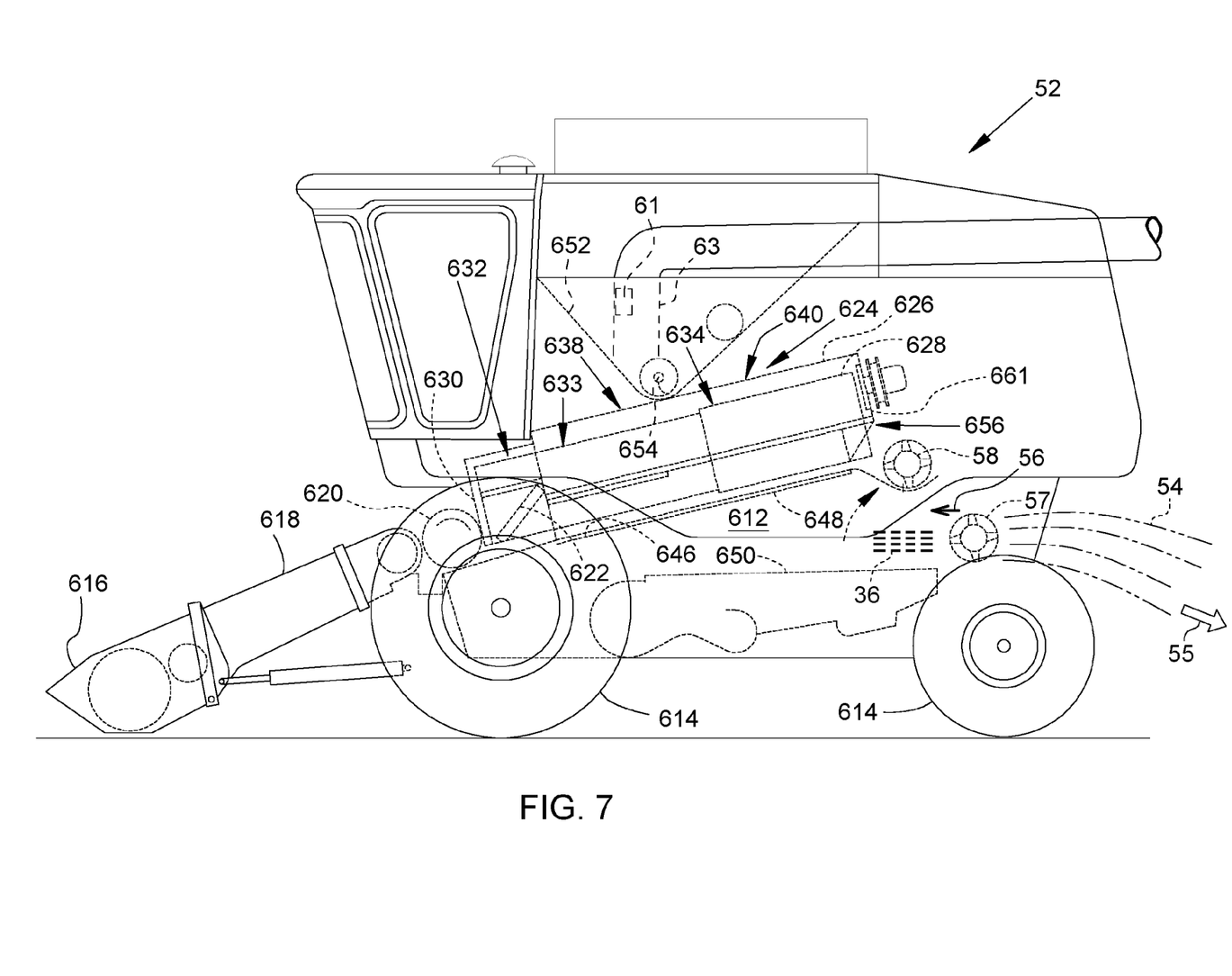
FIG. 7 is a side view of a combine with the exterior of the combine removed to better reveal its internal components and another possible mounting location of the measurement device.

During the calibration mode, the moisture content sensor 61 (e.g., in the clean grain elevator 63 illustrated by dashed lines in FIG. 6 and FIG. 7) may provide an observed reference measurement for the grain and MOG, which tend to have the same or substantially similar moisture content. Alternately, during the calibration mode, in the measurement device 11 the transmitted signal may be transmitted in the range from approximately 900 MHz to approximately 2.4 GHz to estimate the moisture level based on attenuation and/or phase change in the transmitted signal that is received at the receiving antenna or receive patches 32. The moisture content can be used to properly select the observed attenuation; hence, an accurate grain loss estimate that is moisture-adjusted for a particular harvesting session, a particular field, a particular section of the field, or a particular time range.

During an operational mode, when harvested material with material oil content (e.g., grain, seeds, and kernels) is present, at the receiver 34 the transmitted signal (or received signal) is significantly attenuated from the threshold and falls below the attenuation threshold, reference attenuation or reference signal strength. During the operational mode, the phase change between the transmitted signal by the transmitter 10 and the received signal by the receiver 34 can depend upon the following factors: (1) spatial separation or spatial difference between the transmitting antenna and the receiving antenna or conductive patches (26, 28), (2) the frequency or wavelength of the transmitted signal, and (3) any phase change in the transmitted signal (or received signal) induced by the oil content or other properties of the harvested material.

In one configuration, the electronic data processor 42 can estimate the grain loss, or provide an operator alert to a user interface 95 (e.g., electronic display, keyboard, keypad, touch screen display, switches, pointing device, buzzer and/or audio module) coupled to the electronic data processor 42 via data bus 93 and communications port 94 with the grain loss exceeds a threshold, or trigger a control data message for the combine processing system to automatically adjust combine settings of the combine based on the grain loss exceeding a threshold, such as sending a signal to an actuator 97 (e.g., linear actuator or motor, or electrohydraulic cylinder) via vehicle data bus 96 to adjust the clearance between the rotor (e.g., 628 in FIG. 6) and concave (e.g., 646 in FIG. 6) of the kernel processing system or rotary crop processing system 624, or the sieve clearances associated with the cleaning system 650 (e.g., cleaning shoe). The observed attenuation, observed phase change or the transmitted signals received at one or more receivers 34 can vary from sampling interval to sampling interval as field conditions vary, such that adjustments to combine settings can be made in real-time dynamically as the combine traverses a field to harvest crop.

Figure 5:
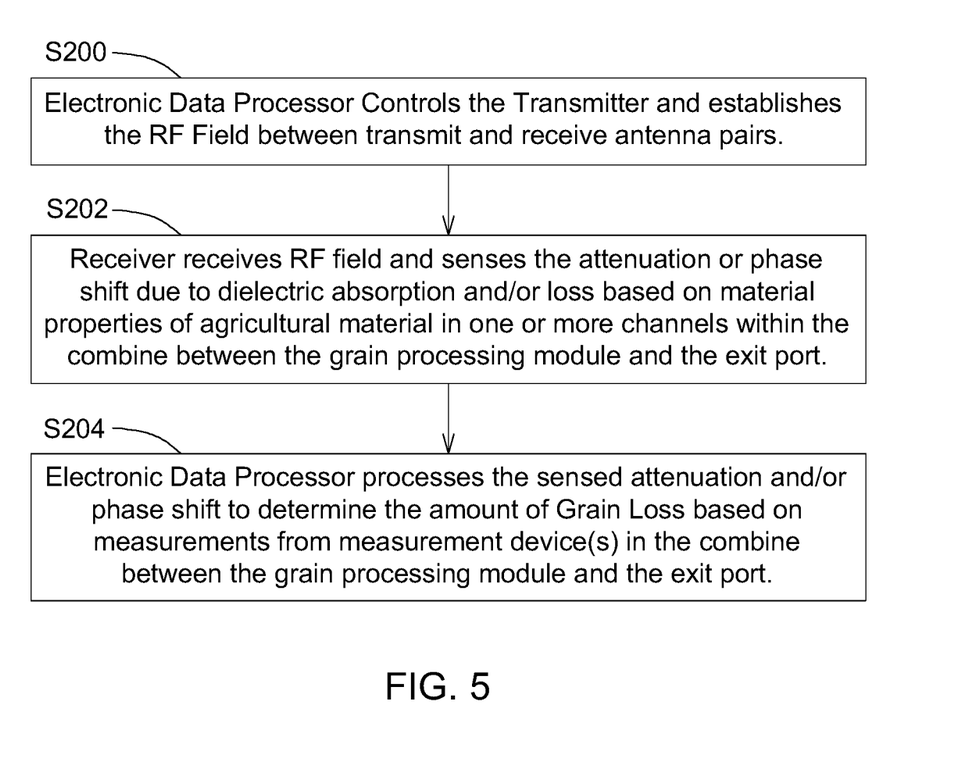
FIG. 5 shows one embodiment of a flow chart for operating the measurement device.

FIG. 5 illustrates one embodiment of a flow chart for a method for measuring grain loss or MOG. The method of FIG. 5 begins in step S200.

In step S200, the measurement device(s) 11 or the electronic data processor 42 controls the transmitter 10 such that the transmitter 10 establishes a radio frequency field between pairs of transmit antennas (e.g., transmit patches 30) and receive antennas (e.g., receive patches 32). For the secondary conductive patches 26 associated with the outer sides 22 of antenna assembly 36, the pairs of transmit antennas (e.g., transmit patches 30) and receive antennas (e.g., receive patches 32) are generally co-planar and positioned on outer sides 22 of the substantially planar members 14, consistent with a secondary radio frequency field 244 or fringing radio frequency field. For the primary conductive patches 28 associated with the inner sides 24 of the substantially planar members 14 or antenna panels 38, the pairs of transmit antennas (e.g., conductive patches 28) and receive antennas (e.g., conductive patches 28) are located on different substantially planar members 14 or different antenna panels 38 that face each other.

In step S202, the measurement device(s) 11 or receiver 34 receives the radio frequency field 44 and senses the attenuation, phase shift, or both caused by dielectric loss based on harvested material properties (e.g., dielectric absorption and/or loss associated with oil content of the grain, or contamination or unexpected grain content in the MOG), as reflected in a reference data 92 or a look-up table stored in data storage device 91, where the measurement device 11 is positioned at one or more locations in the combine 52 after the kernel processing module or grain processing module, or between the kernel processing module and the exit port 54 of the combine 52, such as illustrated in FIG. 6 or FIG. 7, or both.

In step S204, the measurement device(s) 11 or electronic data processor 42 processes the incoming receive signal to determine the amount of grain loss or combine-processing yield loss based on measurements, such as sensed attenuation and/or phase shift, at one or more locations of the antenna assembly 36 in the combine 52 after the kernel processing module or grain processing module, or between the kernel processing module and the exit port 54 of the combine 52.

The measuring device 11 may comprise any embodiment of a measurement device disclosed in this document, or combinations of measurement devices 11, or combinations of antenna assemblies 36 and one or more measurement devices 11, or variations thereof. In one measurement device 11, a set of planar dielectric layers 14 or antenna panels 38 is spaced apart and parallel to each other to provide a channel 16 for agricultural material to flow above, below or between the set of planar dielectric layers 14 or antenna panels 38. Each dielectric planar layer 14 or antenna panel 38 has an upper side 18 and a lower side 20. Conductive patches on the upper side 18 and the lower side 20 of each dielectric layer 14 to form transmitting antennas and corresponding receiving antennas to receive an electromagnetic signal from one or more of the transmitting antennas. A transmitter 10 is coupled to the transmitting antennas. One or more receivers 34 is coupled to the receiving antennas. A detector 40 is associated with the one or more respective receivers 34 for determining or estimating the attenuation of the electromagnetic signal agricultural material in the channel 16. An electronic data processor 42 is arranged for evaluating the estimated attenuation to estimate the grain loss content and material other than grain content of the agricultural material.

As illustrated in FIG. 6, the measurement device 11 or antenna assembly 36 is mounted in a combine 52 toward an exit port 54 of agricultural material from the combine 52 rearward 55 from a straw chopper 57 of the combine 52. In one configuration, a combine 52 or a harvester incorporates the measurement device into a section of the combine 52 that follows a grain processing module that separates grain from the other harvested agricultural material. In one embodiment, the measurement device is arranged for measuring grain loss exiting from an outlet port of the combine 52. For example, the antenna assembly 36 can be configured to occupy an entire internal width, or a portion of the internal width, of the combine 52 or harvester in the tailboard assembly area, such as below a frog-mouth assembly in the tailboard assembly area.

In FIG. 6, the combine 52 comprises a supporting structure or chassis 612 that are supported on the ground by wheels 614 or tracks. A header platform 616 cuts and intakes harvested agricultural material (e.g., standing crop) in the field and directs the harvested agricultural material to a feeder-house 618. The harvested agricultural material is directed by the feeder-house 618 to a beater 620. The beater 620 directs the crop upwardly to a rotary crop-processing unit 624.

The rotary crop-processing unit 624 (e.g., axial rotary crop processing unit) is located within the side walls of the combine, where one side wall in FIG. 6 is removed to better reveal the internal components of the combine 52. The rotary crop-processing unit 624 comprises a rotor housing 626 and a rotatable rotor 628 located within the housing 626. The harvested agricultural material enters the rotor housing 626 through an inlet 622 at the inlet end 630 of the housing 626. The rotor 628 is provided with an inlet feed portion 632, a threshing portion 633, and a separating portion 634. The rotor housing 626 has an inlet end 630, threshing section 638 and a separating section 640.

Both the threshing portion 633 and the separating portion 634 of the rotor are provided with crop-engaging members (not shown). The threshing section 638 of the housing 626 is provided with a concave 646 while the separating section 640 of the housing 626 is provided with a sieve 648. Grain and chaff released from a crop mat or belt fall through the concave 646 and sieve 648. The concave 646 and the sieve 648 prevent the passage of harvested agricultural material larger than grain or chaff from entering the combine cleaning system 650 (e.g., cleaning shoe or sieve assembly) below the rotary crop-processing unit 624.

Grain and chaff, which is processed by the concave 646, falls through the sieve 648 and is directed to the cleaning system 650 that removes the chaff and stover from the grain. The cleaning system 650 directs the grain to an elevator 63 to clean grain tank 652 where it can be directed to a truck or grain cart by unloading auger 654. Straw or stover that reaches the end 661 of the housing 626 is expelled through an outlet 656 to a beater 58. The beater 58 propels the straw, stover and harvested agricultural material out the rear exit port 54 of the combine 52. The harvested agricultural material moves through the rotary crop-processing unit 624 from the inlet end 630 to the outlet end 661 of the housing 626. The operation of the combine is controlled from the operator cab.

As illustrated in FIG. 7, the measurement device or antenna assembly 36 is mounted on a combine 52 frontward 56 from a straw chopper 57 and reward from a chaff discharge zone 59 within the combine 52.

Having described one or more embodiments in this disclosure, it will become apparent that various modifications can be made without departing from the scope of the invention as defined in the accompanying claims. For example, one or more of any dependent claims set forth in this document may be combined with any independent claim to form any combination of features set forth in the appended claims, and such combination of features in the claims are hereby incorporated by reference into the specification of this document.

The following is claimed:

1. A measurement device comprising:
   a transmitter for providing a transmitted signal;
   a signal splitter for splitting the transmitted signal into transmitted signal components;
   a set of planar dielectric layers spaced apart and parallel to each other to provide a channel for agricultural material to flow above or below the set of planar dielectric layers, each dielectric planar member having an upper side and a lower side;
   an outer set of conductive patches on one of a plurality of outer sides of the set of planar dielectric layers, where transmit patches of the outer set of conductive patches are coupled to the transmitter via the signal splitter and where receive patches of the outer set of conductive patches are substantially coplanar with the transmit patches and where the receive patches are coupled to one or more receivers to receive a radio frequency fringing field associated with the transmitted signal of one or more adjacent corresponding transmit patches;
   a detector associated with one or more respective receivers for determining or estimating an attenuation, phase shift, or both of the radio frequency fringing field; and
   an electronic data processing unit for evaluating the estimated attenuation to estimate a grain loss content and material other than grain content of the agricultural material.

2. The measurement device according to claim 1 where the transmit patches are substantially co-planar to the receive patches.

3. The measurement device according to claim 1 where the transmit patches and the receive patches alternate, such that each row in a lateral direction within a harvester is exclusively a transmitting row or a receiving row.

4. The measurement device according to claim 1 further comprising:
   a low pass filter coupled to one or more receivers.

5. The measurement device according to claim 1 wherein the outer set of conductive patches on one of the outer sides of the set of planar dielectric layers further comprises the outer set of conductive patches on an outer upper side of the planar dielectric layers.

6. The measurement device according to claim 1 wherein the outer set of conductive patches on one of the outer sides of the set of planar dielectric layers further comprises the outer set of conductive patches on an outer lower side of the planar dielectric layers.

7. The measurement device according to claim 1 wherein the measurement device is mounted in a combine toward an exit port of agricultural material from the combine rearward from a straw chopper of the combine.

8. The measurement device according to claim 1 wherein the measurement device is mounted on a combine frontward from a straw chopper and reward from a chaff discharge zone within the combine.

9. The measurement device according to claim 1 further comprising:
   the set of planar dielectric layers spaced apart and parallel to each other to provide a primary channel for agricultural material to flow between the set of planar dielectric layers;
   an inner set of conductive patches on a plurality of inner sides of the set of planar dielectric layers, where transmit patches of the inner set of conductive patches are coupled to the transmitter via the signal splitter and where receive patches of the inner set of conductive patches are coupled to one or more receivers to receive a primary radio frequency field, between two adjoining planar dielectric layers of the set, associated with the transmitted signal of one or more adjacent corresponding transmit patches; and the detector associated with one or more respective receivers for determining or estimating an attenuation of the radio frequency fringing field and the primary radio frequency field.

10. A measurement device comprising:

a transmitter for providing a transmitted signal;

a signal splitter for splitting the transmitted signal into transmitted signal components;

a set of planar dielectric layers spaced apart and parallel to each other to provide a primary channel for agricultural material to flow between the set of planar dielectric layers and a secondary channel for agricultural material to flow above or below the set of planar dielectric layers, each dielectric planar member having an upper side and a lower side;

an inner set of primary conductive patches on a plurality of inner sides of the set of planar dielectric layers, where transmit patches of the inner set of primary conductive patches are coupled to the transmitter via the signal splitter and where receive patches of the inner set of primary conductive patches are coupled to one or more receivers to receive a radio frequency field associated with the transmitted signal of one or more adjacent corresponding transmit patches;

an outer set of secondary conductive patches on one of a plurality of outer sides of the set of planar dielectric layers, where transmit patches of the outer set of secondary conductive patches are coupled to the transmitter via the signal splitter and where receive patches of the outer set of secondary conductive patches are coupled to one or more receivers to receive a radio frequency fringing field associated with the transmitted signal of one or more adjacent corresponding transmit patches;

a detector associated with one or more respective receivers for determining or estimating a primary attenuation, phase shift, or both of the received radio frequency field in the primary channel and for determining or estimating a secondary attenuation of the radio frequency fringing field in the secondary channel;

an electronic data processing unit for evaluating the estimated aggregate attenuation, phase shift or both of the primary attenuation and the secondary attenuation to estimate a grain loss content and material other than grain content of the agricultural material.

11. The measurement device according to claim 10 where the transmit patches of or among the primary conductive patches substantially face the receive patches on separate planar dielectric layers.

12. The measurement device according to claim 10 where the outer transmit patches and the outer receive patches, alternate, such that each row in a lateral direction within a harvester is exclusively a transmitting row or a receiving row and wherein the inner transmit patches and the inner receive patches have multiple adjacent rows.

13. The measurement device according to claim 10 further comprising:

a low pass filter coupled to one or more receivers.

14. The measurement device according to claim 10 wherein the inner set of conductive patches on one of the inner sides of the set of planar dielectric layers further comprises the inner set of conductive patches on the inner upper side of the planar dielectric layers.

15. The measurement device according to claim 10 wherein the inner set of conductive patches on one of the inner sides of the set of planar dielectric layers further comprises the inner set of conductive patches on the lower side of the planar dielectric layers.

16. The measurement device according to claim 10 wherein the measurement device is mounted in a combine toward an exit port of agricultural material from the combine rearward from a straw chopper of the combine.

17. The measurement device according to claim 10 wherein the measurement device is mounted on a combine frontward from a straw chopper and reward from a chaff discharge zone within the combine.

18. A combine comprising:

a measurement device for measuring grain loss exiting from an outlet port at a rear of the combine;

the measuring device comprising:

a set of planar dielectric layers spaced apart and parallel to each other to provide a primary channel for agricultural material to flow between the set of planar dielectric layers, each dielectric planar member having an upper side and a lower side;

a plurality of conductive patches on the upper side and the lower side of each dielectric layer to form transmitting antennas and corresponding receiving antennas to receive an electromagnetic signal from one or more of the transmitting antennas;

a transmitter coupled to the transmitting antennas;

one or more receivers coupled to the receiving antennas;

a detector associated with the one or more respective receivers for determining or estimating the attenuation of the electromagnetic signal through the agricultural material in the primary channel; and an electronic data processing unit for evaluating the estimated attenuation of the electromagnetic signal in the primary channel to estimate a grain loss content and material other than grain content of the agricultural material.

19. The combine according to claim 18 wherein the measurement device is mounted in a combine toward an exit port of agricultural material from the combine rearward from a straw chopper of the combine.

20. The measurement device according to claim 18 wherein the measurement device is mounted on a combine frontward from a straw chopper and reward from a chaff discharge zone within the combine.

\* \* \* \* \*